United States Patent
Yodfat et al.

(10) Patent No.: US 8,845,613 B2
(45) Date of Patent: Sep. 30, 2014

(54) BOLUS DOSE DETERMINATION FOR A THERAPEUTIC FLUID DISPENSING SYSTEM

(75) Inventors: Ofer Yodfat, Modi'in (IL); Gali Shapira, Haifa (IL)

(73) Assignee: Roche Diagnostics Operations, Inc., Indianapolis, IN (US)

(*) Notice: Subject to any disclaimer, the term of this patent is extended or adjusted under 35 U.S.C. 154(b) by 872 days.

(21) Appl. No.: 12/865,042

(22) PCT Filed: Jan. 28, 2009

(86) PCT No.: PCT/IL2009/000104
§ 371 (c)(1),
(2), (4) Date: Nov. 4, 2010

(87) PCT Pub. No.: WO2009/095908
PCT Pub. Date: Aug. 6, 2009

(65) Prior Publication Data
US 2011/0054439 A1    Mar. 3, 2011

Related U.S. Application Data

(60) Provisional application No. 61/024,117, filed on Jan. 28, 2008.

(51) Int. Cl.
*A61M 31/00* (2006.01)
*A61M 5/142* (2006.01)
*A61M 5/172* (2006.01)
*G06F 19/00* (2011.01)

(52) U.S. Cl.
CPC . *A61M 5/14248* (2013.01); *A61M 2005/14296* (2013.01); *A61M 5/1723* (2013.01); *A61M 2230/201* (2013.01); *A61M 2205/3592* (2013.01); *A61M 2005/14268* (2013.01); *G06F 19/3468* (2013.01)
USPC ............... 604/504; 604/503; 604/65; 604/66; 604/67

(58) Field of Classification Search
USPC ................. 604/503, 504, 65, 66, 67
See application file for complete search history.

(56) References Cited

U.S. PATENT DOCUMENTS 6,936,029 B2    8/2005    Mann et al.
2005/0118326 A1*    6/2005    Anfinsen et al. .............. 426/658

(Continued)

FOREIGN PATENT DOCUMENTS

WO    WO 2008009737 A2 *    1/2008
WO    WO 2008/078318 A2    7/2008

(Continued)

OTHER PUBLICATIONS

Wolever et al, Food glycemic index, as given in Glycemic Index tables, is a significant determinant of glycemic responses elicited by composite breakfast meals, 2006, The American Journal of Clinical Nutrition, 83, 1306-12.*

(Continued)

*Primary Examiner* — Kami A Bosworth
*Assistant Examiner* — Shefali Patel
(74) *Attorney, Agent, or Firm* — Roche Diagnostics Operations, Inc.

(57) ABSTRACT

Disclosed is a medical device to treat diabetes. The medical device includes a bolus calculator to determine an insulin bolus based on, at least in part, a glycemic index value associated with an intake to be consumed by a user, the bolus calculator further adapted to determine the insulin bolus using one or more inputs selected from the group consisting of a carbohydrate load of the intake, a current glucose level of the user, a residual insulin of the user, a carbohydrate to insulin ration, an insulin sensitivity of the user and a target glucose level of the user. The bolus calculator is housed in one or more of, for example, an insulin dispensing pump, a handheld remote control unit for the insulin dispensing pump and/or a handheld glucose monitor.

20 Claims, 13 Drawing Sheets

(56) References Cited

U.S. PATENT DOCUMENTS

| | | | |
|---|---|---|---|
| 2007/0106218 A1 | 5/2007 | Yodfat et al. | |
| 2007/0112298 A1* | 5/2007 | Mueller et al. | 604/65 |
| 2007/0191702 A1 | 8/2007 | Yodfat et al. | |
| 2008/0171967 A1* | 7/2008 | Blomquist et al. | 604/67 |
| 2008/0214916 A1 | 9/2008 | Yodfat et al. | |
| 2008/0215035 A1 | 9/2008 | Yodfat et al. | |

FOREIGN PATENT DOCUMENTS

| | | |
|---|---|---|
| WO | WO 2008/078319 A1 | 7/2008 |
| WO | WO 2009/125398 A2 | 10/2009 |

OTHER PUBLICATIONS

DCCT Trial, N. Engl J. Med 1993; 329: 977-986.
UKPDS Trial, Lancet 1998; 352: 837-853.
BMJ 1998; 317, (7160): 703-13.
EDIC Trial, N Engl J Med 2005; 353, (25): 2643-53.
Am J Clin Ntr 2006; 83; 1306-12.
International Search Report for International Application No. PCT/IL2009/000104, date of mailing Sep. 15, 2009.
Written Opinion of the International Application No. PCT/IL2009/000104, date of mailing Sep. 15, 2009.

* cited by examiner

| Total daily insulin dose (TDD) [IU/day] | 2200 Rule [mg\dL] | 2000 Rule [mg\dL] | 1800 Rule [mg\dL] | 1600 Rule [mg\dL] |
|---|---|---|---|---|
| 20 | 110 | 100 | 90 | 80 |
| 25 | 88 | 80 | 72 | 64 |
| 30 | 73 | 67 | 60 | 53 |
| 35 | 63 | 57 | 51 | 46 |
| 40 | 55 | 50 | 45 | 40 |
| 50 | 44 | 40 | 36 | 32 |
| 60 | 37 | 33 | 30 | 27 |
| 75 | 29 | 27 | 24 | 21 |
| 100 | 22 | 20 | 18 | 16 |

INSULIN SENSITIVITY TABLE GRID, POINT DROP PER UNIT OF INSULIN

*FIG 1*

| Total daily insulin dose (TDD) [IU/day] | 500 Rule [gram] | 450 Rule [gram] |
|---|---|---|
| 20 | 25 | 23 |
| 25 | 20 | 18 |
| 30 | 17 | 15 |
| 35 | 14 | 13 |
| 40 | 13 | 11 |
| 50 | 10 | 9 |
| 60 | 8 | 8 |

CARB TO INSULIN RATIO, CARBS COVERED BY 1 UNIT OF INSULIN

*FIG 2*

| DOSE GIVEN [IU] | UNITS LEFT TO WORK AFTER: | | | | |
| --- | --- | --- | --- | --- | --- |
| | 1 Hr | 2 Hr | 3 Hr | 4 Hr | 5 Hr |
| 1 | 0.8 | 0.6 | 0.4 | 0.2 | 0 |
| 2 | 1.6 | 1.2 | 0.8 | 0.4 | 0 |
| 3 | 2.4 | 1.8 | 1.2 | 0.6 | 0 |
| 4 | 3.2 | 2.4 | 1.6 | 0.8 | 0 |
| 5 | 4.0 | 3.0 | 2.0 | 1.0 | 0 |
| 6 | 4.8 | 3.6 | 2.4 | 1.2 | 0 |
| 7 | 5.6 | 4.2 | 2.8 | 1.4 | 0 |
| 8 | 6.4 | 4.8 | 3.2 | 1.6 | 0 |
| 9 | 7.2 | 5.4 | 3.6 | 1.8 | 0 |
| 10 | 8.0 | 6.0 | 4.0 | 2.0 | 0 |

INSULIN RESIDUE, INSULIN UNITS LEFT TO WORK

*FIG 3*

| Cereals | | Snacks | | Pasta | | Beans | |
|---|---|---|---|---|---|---|---|
| All Bran | 51 | chocolate bar | 49 | cheese tortellini | 50 | Baked | 44 |
| Bran Buds + psyll | 45 | corn chips | 72 | fettucini | 32 | black beans, boiled | 30 |
| Bran Flakes | 74 | croissant | 67 | linguini | 50 | butter, boiled | 33 |
| Cheerios | 74 | doughnut | 76 | macaroni | 46 | cannellini beans | 31 |
| Corn Chex | 83 | graham crakers | 74 | spagh, 5 min boiled | 33 | garbanzo, boiled | 34 |
| Cornflakes | 83 | jelly beans | 80 | spagh, 15 min boiled | 44 | kidney, boiled | 29 |
| Cream of Wheat | 66 | Life Savers | 70 | spagh, prot enrich | 28 | kidney, canned | 52 |
| Frosted Flakes | 55 | oatmeal cookie | 57 | vermicelli | 35 | lentils, green, brown | 30 |
| Grapenuts | 67 | pizza, cheese & tom | 60 | Soups/Vegetables | | lima, boiled | 32 |
| Life | 66 | Pizza Hut, supreme | 33 | beets, canned | 64 | navy beans | 38 |
| muesli, natural | 54 | popcorn, light micro | 55 | black bean soup | 64 | pinto, boiled | 39 |
| Nutri-grain | 66 | potato chips | 56 | carrots, fresh, boil | 49 | red lentils, boiled | 27 |
| oatmeal, old fash | 48 | pound cake | 54 | corn, sweet | 56 | soy, boiled | 16 |
| Puffed Wheat | 67 | Power bars | 58 | french fries | 75 | Breads | |
| Raisin Bran | 73 | pretzels | 83 | grean pea, soup | 66 | bagel, plain | 72 |
| Rice Chex | 89 | saltine crakers | 74 | green pea, frozen | 47 | baquette, Frnch | 95 |
| Shredded Wheat | 67 | shortbread cookies | 64 | lima beans, frozen | 32 | Croissant | 67 |

*FIG 4a*

CONTINUATION OF TABLE 4a

| Special K | 54 | Snickers bar | 41 | parsnips | 97 | dark rey | 76 |
|---|---|---|---|---|---|---|---|
| Total | 76 | strawberry jam | 51 | peas, fresh, boil | 48 | Hamburger bun | 61 |
| Fruit | | vanilla wafers | 77 | pot, new, boiled | 59 | Muffins | |
| apple | 38 | Wheat Thins | 67 | pot, red, baked | 93 | apple, cin | 44 |
| apricots | 57 | Crackers | | pot, sweet | 52 | Blueberry | 59 |
| banana | 56 | graham | 74 | pot, white, boiled | 63 | oat & raisin | 54 |
| cantalope | 65 | rice cakes | 80 | pot, white, mashed | 70 | Pita | 57 |
| cherries | 22 | rye | 68 | split pea soup w/ham | 66 | pizza, cheese | 60 |
| dates | 103 | soda | 72 | tomato soup | 38 | pumpernickel | 49 |
| grapefruit | 25 | Wheat Thins | 67 | yam | 54 | Sourdough | 54 |
| grapes | 46 | Cereal Grains | | Milk Products | | Rye | 64 |
| kiwi | 52 | barley | 25 | chocolate milk | 35 | White | 70 |
| mango | 55 | basmati white rice | 58 | custard | 43 | Wheat | 68 |
| orange | 43 | bulgar | 48 | ice cream, van | 60 | Drinks | |
| papaya | 58 | couscous | 65 | ice milk, van | 50 | apple juice | 40 |
| peach | 42 | cornmeal | 68 | skim milk | 32 | colas | 65 |
| pear | 58 | millet | 71 | soy milk | 31 | Gatorade | 78 |
| pineapple | 66 | | | tofu frozen dessert | 115 | grapefruit juice | 48 |
| plums | 39 | fructose | 22 | whole milk | 30 | orange juice | 46 |
| prunes | 15 | honey | 62 | yogurt, fruit | 36 | pineapple juice | 46 |
| raisins | 64 | maltose | 105 | yogurt, plain | 14 | | |
| watermelon | 72 | table sugar | 64 | | | | |

*FIG 4b*

GI (ACQUIRED FROM DIABETES MALL AT DIABETESNET.COM)

BOLUS DOSE DETERMINATION FOR A THERAPEUTIC FLUID DISPENSING SYSTEM

CROSS-REFERENCE TO RELATED APPLICATIONS

The application is a §371 national stage filing of PCT application no. PCT/IL2009/000104, international filing date of Jan. 28, 2009, which claims priority to provisional U.S. application Ser. No. 61/024,117, entitled, "Bolus Dose Calculation For a Therapeutic Fluid Dispensing System," filed Jan. 28, 2008. The content of each application is hereby incorporated by reference in its entirety.

BACKGROUND

The present disclosure relates generally to a method and a device for infusion of fluids.

Diabetes mellitus is a disease of major global importance, increasing in frequency at almost epidemic rates such that the worldwide prevalence in 2006 is approximately 170 million people and is predicted to at least double over the next 10-15 years. Diabetes is characterized by a chronically raised blood glucose concentration (hyperglycemia) due to a relative or absolute lack of the pancreatic hormone insulin. Within the healthy pancreas, beta cells, located in the islets of Langerhans, continually produce and secrete insulin according to the blood glucose levels, maintaining a near constant glucose levels in the body.

Much of the burden of the disease to the patient and to health-care resources is due to the long-term tissue complications, which affect both the small blood vessels (microangiopathy, causing eye, kidney and nerve damage) and large blood vessels (causing accelerated atherosclerosis, with increased rates of coronary heart disease, peripheral vascular disease and stroke).

The Diabetes Control and Complications Trial (DCCT) demonstrated that development and progression of the chronic complications of diabetes are greatly related to the degree of altered glycemia as quantified by determinations of glycohemoglobin (HbA1c). (See, for example, DCCT Trial, N Engl J Med 1993; 329: 977-986, UKPDS Trial, Lancet 1998; 352: 837-853. BMJ 1998; 317, (7160): 703-13 and the EDIC Trial, N Engl J Med 2005; 353, (25): 2643-53.) Thus, it is important to maintain euglycemia by performing frequent glucose measurements and by making adjustments of insulin delivery accordingly.

Insulin pumps can be used for measurement and adjustment of insulin delivery. Some insulin pumps deliver rapid acting insulin 24 hours a day through a catheter placed under the skin. The total daily insulin dose can be divided into basal and bolus doses. Basal insulin can be delivered continuously and/or periodically over a 24-hour period to keep the blood glucose levels in range between meals and overnight. Diurnal basal rates can be pre-programmed or manually changed according to various daily activities. Insulin boluses can be delivered before meals or during episodes of high blood sugar levels to counteract carbohydrates loads.

Insulin pumps can compute a bolus dose using several parameters. For example, insulin pumps can use any of the following parameters:
Amount of carbohydrates (Carbs) to be consumed, alternatively defined as "servings", where one (1) serving equal approximately 15 grams of Carbs;
Carbohydrate-to-Insulin ratio (CIR), i.e., the amount of carbohydrates balanced by one unit of insulin;
Insulin sensitivity (IS), i.e., the amount of blood glucose value lowered by one unit of insulin;
Current blood glucose level (CBG);
Target blood glucose level (TBG), i.e., the desired blood glucose level. TBG for most people suffering from diabetes is in the range of 90-130 mg/dL.
Residual insulin (RI), i.e., the amount of stored insulin remaining in the body after recent delivery of still active boluses. This parameter is relevant when there is a short time interval between consecutive boluses (e.g., less than 5 hours).

In U.S. Pat. No. 6,936,029, a pump provided with a bolus calculator and a procedure to calculate the amount of insulin to be administered is described. The procedure is based on the following formula for calculating a bolus:

$$\text{Recommended bolus} = \underbrace{(TC/CIR)}_{\text{"Food estimate"}} + \underbrace{(CBG-TBG)/IS - RI}_{\text{"Correction estimate"}}$$

where TC is the total amount of carbohydrates, CIR is the carbohydrate-to-insulin ratio, TBG is the target blood glucose, CBG is the current blood glucose, IS is the insulin sensitivity and RI is the remaining insulin (i.e., "residual insulin").

The insulin sensitivity (IS) may be determined, for example, according to the "2200 to 1600 rules" commonly used by type 1 diabetes patients using rapid acting insulin (e.g., Humalog®, Novolog®). Specifically, the user's IS can be determined by dividing the value corresponding to an appropriate Rule (i.e., a standard value, such as 1800, which is divided by a daily insulin dose to compute an estimated insulin sensitivity for the patient) by the total daily dose of rapid-acting insulin (e.g., if the total daily insulin dose is 40 units and the 1800 rule is used, the insulin sensitivity factor would be 1800 divided by 40=45 mg/dl/unit). For example, the table of FIG. 1 shows the point drop per unit of insulin (insulin sensitivity) corresponding to various rules (adapted from Using Insulin© 2003)

The carbohydrate to insulin ratio (CIR) may be determined, for example, according to the "450 to 500 rules" commonly used by type 1 diabetes patients using rapid acting insulin (e.g. Humalog®, Novolog®). The user's CIR can be determined by dividing the value corresponding to an appropriate Rule by the total daily dose of rapid-acting insulin (e.g., if the total daily insulin dose is 40 units and the 450 Rule is used, the carbohydrate to insulin ratio (CIR) would be 450 divided by 40=11 gram). The table in FIG. 2 shows carbs (in grams) covered by 1 unit of insulin (CIR ratio) according to the various Rules (adapted from Using Insulin© 2003).

The residual insulin can be determined according to the pharmacokinetics of rapid acting insulin (e.g., Humalog®, Novolog®). The table in FIG. 3 provides the units of residual insulin 1-5 hours after the most recent administration of a bolus dose (adapted from Using Insulin© 2003).

Currently available insulin pumps generally do not use the glycemic index (GI) or glycemic indexes of the carbohydrates of the intake to determine the bolus dosage. GI is a ranking system for carbohydrates based on their effect on blood glucose levels. According to this system, glucose, the fastest-acting carbohydrate, is given a value of 100, and other carbs are ranked relative to that measurement. Ripeness, cooking time, fiber, and fat content can all impact how a food affects the blood glucose (BG). A low GI food will release glucose more slowly and steadily. A high GI food causes a more rapid rise in blood glucose levels. The table in FIG. 4 lists different types of foods and their respective GI's.

SUMMARY

In some embodiments, an insulin dispensing device and a method to calculate appropriate insulin bolus dosage based on, at least in part, the GI of the intake food is provided.

Techniques are provided for a dispensing device that can deliver therapeutic fluid (e.g., insulin) in accordance with the glycemic index of the intake. In one aspect, the dispensing device can be implemented using a bolus calculator. In some embodiments, the bolus calculator can be configured to compute an insulin bolus as a function of glycemic index of the intake. It can also be configured to determine the insulin bolus using one or more inputs, such as carbohydrate load of the intake, current blood glucose, insulin residue, carbohydrate to insulin ratio, insulin sensitivity of a user, target blood glucose of the user, and other parameters germane to the computation of the insulin bolus.

The dispensing device (also referred to as a fluid delivery device) includes, in some embodiments, a dispensing patch unit and, in some embodiments, a remote control unit which can communicate with the dispensing patch unit and enable programming and specification of therapeutic fluid delivery operations, receipt of user input and data acquisition. In some embodiments, programming and specifications of instructions and operations for performance by the dispensing device can be performed manually by operating buttons located on the dispensing patch unit. In some implementations, the dispensing patch unit is composed of two parts—a disposable part and a reusable part. The disposable part can contain a reservoir and an outlet port. The reusable part generally includes the electronic circuitry of the device (PCB, processor, etc), the driving mechanism, metering portion, and other components/modules/units that are relatively more expensive. In some embodiments, a cradle unit can be provided in a form of a flat plate that can be secured to (e.g., adhered) to the skin to enable patch disconnection and reconnection at the patient's discretion. After attachment of the cradle unit to the skin, a cannula can be inserted into the subcutaneous compartment through a dedicated passageway in the cradle unit. The fluid delivery device can comprise a module to determine an appropriate bolus dose in accordance with, at least in part, the glycemic index (GI) of the intake.

In some embodiments, a device that employs a method for calculation of appropriate insulin bolus doses in accordance with, at least in part, the glycemic index of the intake is provided. Such a method can be used with a device dedicated only for determination (computation) of the appropriate bolus. It can also be implemented in a glucometer, a continuous glucose monitor, an infusion pump, a delivery pen, a personal computer (PC) or any other device used by the diabetes patient.

In some embodiments, a device that dispenses insulin and performs a procedure for the determination of appropriate insulin bolus doses based on, at least in part, the glycemic index of the intake is provided. In some embodiments, a device to monitor glucose concentration levels and dispense insulin boluses according to, at least in part, a GI based bolus computations is provided.

In some embodiments, a device that continuously and/or periodically monitors body glucose levels and can concomitantly deliver insulin boluses according to, at least in part, GI-based bolus computations is described. In some embodiments, a device, which is miniature, discreet, economical for the users and cost effective, and which employs a GI-based bolus determination module is provided.

In some embodiments, a device comprising a miniature skin securable (e.g., adherable) insulin dispensing patch that can deliver insulin boluses according to a GI-based bolus calculation is described.

In some embodiments, a device that includes a skin adherable dispensing patch unit and a method to calculate an insulin bolus in accordance with, at least in part, glycemic index of an intake is provided. The dispensing patch unit can be attached to the skin directly, or by using a cradle unit. In some embodiments, a device with a dispensing patch unit that can be disconnected and reconnected, and a method to calculate an insulin bolus in accordance with the glycemic index of the intake are provided.

In some embodiment, a device comprising a miniature skin securable (e.g., adherable) patch that can continuously and/or periodically dispense insulin and monitor body glucose concentration levels, and a method to determine an insulin bolus dosage in accordance with, at least in part, glycemic index of an intake are provided.

In some embodiments, a device that dispenses insulin according to monitored glucose levels and a method to calculate an insulin bolus in accordance with the glycemic index of an intake is provided. In some implementations, a device that contains an insulin dispensing patch unit comprising a disposable part and a reusable part is described. The reusable part may contain the relatively expensive components/parts of the unit and the disposable part can contain the relatively inexpensive components/parts of the unit, thus providing a relatively low cost product. The device described herein can also perform a procedure to determine an insulin bolus in accordance with glycemic index of an intake.

In some embodiments, a device that comprises insulin dispensing patch unit that can be remotely controlled and a method to determine an insulin bolus in accordance with glycemic index of an intake are provided.

In some embodiments, method(s) for calculating a bolus can be based on the following parameters: current blood glucose levels (BG), carbohydrate load of the intake (Carb), glycemic index (or indices) of the intake (GI) or glycemic load/s of the intake (GL), insulin sensitivity of the user (IS), carbohydrate to insulin ratio (CIR) of the user and residual insulin (RI).

In some implementations, the glycemic index of a meal comprising more than one food type can be determined according to the following equation (as described, for example, in *Am J Clin Nutr* 2006; 83:1306-12):

$$GI = \frac{\sum_{a=1}^{n} GI_a * Carb_a}{Carb} \tag{1}$$

where GI corresponds to the glycemic index of the entire meal, n is the number of carbohydrate-containing foods in the meal, $GI_a$ is the GI of the $a^{th}$ food, carb is the carbohydrate load of the entire meal and $carb_a$ is the carbohydrate load of the $a^{th}$ food.

In some embodiments, the bolus dose can be determined according to the relationship (as described, for example, in *Am J Clin Nutr* 2006; 83:1306-12):

$$Bolus = \frac{RIR}{100} * \frac{carb}{CIR} + \frac{CBG - TBG}{IS} - RI \qquad (2)$$

where $$RIR = 2.9*(0.6*GI + 0.003*GI^2)*(1 - e^{-0.0078*carb}) + 5 \qquad (3)$$

and where
  RIR refers to the relative insulinemic response, i.e., the insulinemic response resulting from a meal, expressed as a percentage of the insulinemic response after ingestion of a known amount (50 g) of available carbohydrate from the GI reference food (e.g., glucose);
  CIR refers to the carbohydrate to insulin ratio of the user;
  IS refers to the insulin sensitivity of the user;
  CBG refers to the current blood glucose of the user;
  TBG refers to the target blood glucose of the user;
  RI refers to the residual insulin from previous boluses;
  GI refers to the glycemic index of the entire meal; and
  Carb refers to the carbohydrate load of the entire meal.

According to some embodiments, the equation for RIR can be altered to be relative to a different amount of reference carbs (i.e., not necessarily 50 g glucose). The recommended bolus dose can be automatically calculated upon inputs of BG levels, carbohydrate load, and GI or GL.

In some embodiments, the user accepts automatically calculated recommended bolus and causes a bolus dosage corresponding to the recommended amount to be accordingly delivered. The automatically calculated bolus can be delivered without providing a user interface notification to the user. In such embodiments, the user can be notified prior to bolus administration and can suspend delivery or select an alternative dose.

In some embodiments, GI-based bolus determination procedures may be implemented in an insulin infusion device comprising an insulin dispensing patch unit and a remote control unit, where a glucose sensing apparatus (e.g., glucometer) is integrated into the remote control unit. In some embodiments, the dispensing patch unit can be composed of two parts, a reusable part that contains, for example, the electronic circuitry, driving mechanism, and other relatively expensive components, and a disposable part that includes, for example, an insulin reservoir, a power supply, and generally the relatively inexpensive components of the dispensing patch unit. The glucose sensing apparatus (e.g., glucometer) may alternatively be integrated in the reusable part of the patch unit of the device.

The GI-based bolus calculator can be implemented in the remote control unit of the insulin infusion device. The GI dependent bolus calculator can also be implemented in the reusable part of the dispensing patch unit of the device. Alternatively, the GI-based bolus calculator can be implemented in both the reusable part of the dispensing patch unit of the device and the remote control unit of the device.

In some embodiments, the GI-based bolus calculator can be implemented in the dispensing patch unit that continuously and/or periodically monitors body glucose levels and can concomitantly deliver insulin into the body. The dispensing patch unit may include a reusable part and a disposable part. The insulin dispensing and glucose sensing functionalities can be combined into a semi closed loop system such that a controller (e.g., processor-based controller) apparatus regulates the dispensing of basal insulin according to the sensed glucose concentration. The meal boluses can be controlled by the GI-based bolus calculator.

The GI dependent bolus calculator can also be implemented in the remote control unit of the device. Alternatively, the GI dependent bolus calculator can be implemented in the reusable part of dispensing patch unit of the device, or in both the reusable part of the dispensing patch unit of the device and the remote control unit of the device.

In some embodiments, the GI-based bolus calculation method can be implemented in a device for sensing blood glucose (e.g., glucometer) or a device for continuously and/or periodically sensing subcutaneous interstitial fluid glucose or for any other glucose sensing device (e.g., non-invasive glucose sensors, iontophoresis based sensors, etc.)

Articles are also described that comprise a machine-readable medium embodying instructions that when performed by one or more machines result in operations described herein. Similarly, computer systems are also described that may include a processor and a memory coupled to the processor. The memory may store one or more programs that cause the processor to perform one or more of the operations described herein.

In one aspect, a medical device to treat diabetes is disclosed. The medical device includes a bolus calculator to determine an insulin bolus based on, at least in part, a glycemic index value associated with an intake to be consumed by a user, the bolus calculator further adapted to determine the insulin bolus using one or more inputs selected from the group consisting of carbohydrate load of the intake, current glucose level of the user, residual insulin of the user, carbohydrate to insulin ratio, insulin sensitivity of the user and target glucose level of the user. The bolus calculator is housed in one or more of, for example, an insulin dispensing pump, a handheld remote control unit for an insulin dispensing pump and/or a handheld glucose monitor.

Embodiments of the device may include one or more of the following features.

The medical device may further include the insulin dispensing pump to dispense insulin to the user.

The medical device may be further adapted to monitor glucose levels of the user.

The medical device may further include the insulin dispensing pump. The insulin dispensing pump may be configured as a closed loop system such that insulin is dispensed based on one or more of, for example, the monitored glucose levels of the user, the insulin bolus determined by the calculator and/or any one of the one or more inputs.

The calculator may be further adapted to determine the insulin bolus using glucose levels monitored by the device.

The medical device may be securable to the user's skin and may be configured to dispense insulin.

The medical device may further include a removable dispensing unit.

The medical device may further include the insulin dispensing pump, and a cradle unit to receive the insulin dispensing pump. The cradle unit may be securable to the skin of the user, and the dispensing pump may be adapted to be connected to and disconnected from the cradle unit. The dispensing pump may be controllable by the remote control unit. The bolus calculator may be implemented in the remote control unit.

The medical device may further include the insulin dispensing pump, the insulin dispensing pump being skin securable and adapted to dispense insulin and monitor body glucose levels.

The calculator may be adapted to determine the insulin bolus based on the relationship:

$$Bolus = \frac{RIR}{100} * \frac{carb}{CIR} + \frac{CBG - TBG}{IS} - RI$$

where RIR is the relative insulinemic response computed based on the relationship:

$$RIR = 2.9*(0.6*GI + 0.003*GI^2)*(1 - e^{-0.0078*carb}) + 5$$

and where CIR is the carbohydrate to insulin ratio of the user, IS is the insulin sensitivity of the user, CBG is the current glucose level of the user, TBG is the target glucose of the user, RI is the residual insulin from previous insulin administration to the user, GI is the glycemic index of the intake, and Carb is the carbohydrate load of the intake.

The calculator may be adapted to compute a composite glycemic index corresponding to a composite intake comprising two or more dietary components based on the respective indices and carbohydrate loads of the two or more dietary components. The calculator adapted to compute the composite glycemic index may be adapted to compute the composite glycemic index according to the relationship:

$$GI = \frac{\sum_{a=1}^{n} GI_a * Carb_a}{Carb}$$

where GI is the composite glycemic index for the composite intake, n is the number of carbohydrate-containing dietary components in the composite intake, $GI_a$ is an individual glycemic index GI of an $a^{th}$ dietary component, carb is a carbohydrate load of the entire composite intake and $carb_a$ is an individual carbohydrate load of the $a^{th}$ component of the composite intake.

The calculator may include a processor to perform computations to determine the insulin bolus, and a user interface to perform one or more of, for example, enter data corresponding to one or more of the inputs and/or display data of at least one of the determined insulin bolus and one or more of the inputs.

The current glucose level may include one or more of, for example, blood glucose level of the user and glucose level in interstitial fluids of the user.

In another aspect, a method for dispensing an insulin bolus is disclosed. The method includes determining a glycemic index of a dietary intake, determining the insulin bolus based on the glycemic index of the dietary intake and one or more inputs selected from the group consisting of carbohydrate load of the intake, current glucose level of a user, residual insulin, carbohydrate to insulin ratio, insulin sensitivity of a user and target glucose of the user. The method further includes dispensing the determined insulin bolus into the user.

Embodiments of the method may include one or more of the features described above in relation to the device, as well as any of the following features.

The method may further include monitoring the glucose levels of the user.

The method may further include dispensing insulin in a closed loop system such that insulin is dispensed based on one or more of, for example, the monitored glucose level input of the user, the determined insulin bolus and/or any one of the one or more inputs.

The glycemic index of the intake may be retrieved from a database.

The method may further include housing a bolus calculator to determine the insulin bolus in one or more of, for example, an insulin dispensing pump, a handheld remote control unit for an insulin dispensing pump and/or a handheld glucose monitor.

In a further aspect, a method for dispensing an insulin bolus is disclosed. The method includes receiving a glucose level value, a carbohydrate load value and a glucose index value, determining the insulin bolus based on the glucose level value, carbohydrate load value and glucose index value, and dispensing the determined insulin bolus into a body of a user.

Embodiments of the method may include one or more of the features described above in relation to the device and method, as well as any of the following features.

The method may further include providing a notification about the determined insulin bolus to the user. Notification may be provided to a remote control unit configured to control an insulin dispensing patch unit. The remote control unit may be housed in one of, for example, a watch, a cellular phone, a personal digital assistant and/or a laptop.

The glucose level value may be received from a glucose monitoring apparatus.

The method may further include dispensing insulin in a closed loop system such that insulin is dispensed based on one or more of, for example, the monitored glucose level, the determined insulin bolus, the carbohydrate load value and/or the glucose index value. The glucose monitoring apparatus may be periodically transmitting the glucose value.

The glucose level value may be received from the user.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

FIG. 1 is an insulin sensitivity table grid showing point drop per unit of insulin.

FIG. 2 is a table of Carbs-to-Insulin ratio for two different insulin sensitivity Rules.

FIG. 3 illustrates insulin activity at 1, 2, 3, 4, and 5 hours after insulin bolus administration.

FIGS. 4*a* and 4*b* are a table listing the respective glycemic indices (GI) for different types of foods.

DETAILED DESCRIPTION

Figure 5:
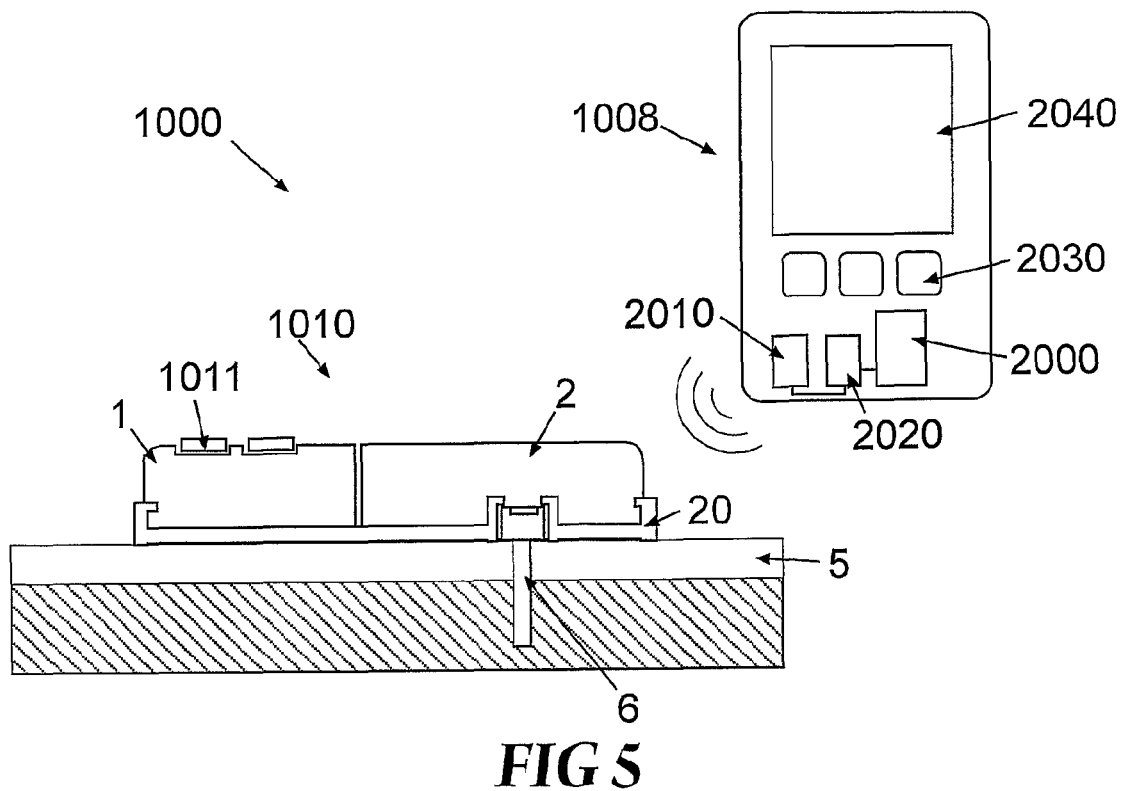
FIG. 5 is a schematic diagram of an exemplary insulin infusion device.

Disclosed is a medical device to treat diabetes. The medical device includes a bolus calculator to determine an insulin bolus based on, at least in part, a glycemic index value associated with an intake to be consumed by a user. The bolus calculator is further adapted to determine the insulin bolus using one or more inputs that include, for example, a carbohydrate load of the intake, current glucose level of the user, residual insulin of the user, carbohydrate to insulin ratio, insulin sensitivity of the user and/or target glucose level of the user. The bolus calculator is housed in one or more of, for example, an insulin dispensing pump, a handheld remote control unit for an insulin dispensing pump and/or a handheld glucose monitor. Also disclosed is a method for dispensing an insulin bolus. The method includes determining a glycemic index of a dietary intake, determining the insulin bolus based on the glycemic index of the dietary intake and one or more inputs that include, for example, carbohydrate load of the intake, current glucose level of a user, residual insulin, carbohydrate to insulin ratio, insulin sensitivity of a user and/or target glucose of the user. The method further includes dispensing the determined insulin bolus into the user.

As described herein, a dispensing device that can deliver therapeutic fluid (e.g., insulin) in accordance with, at least in part, the glycemic index of an intake is provided. In one aspect, the dispensing device includes a module, referred to as a bolus calculator, to determine the bolus dosage based, at least in part, on the glycemic index of the intake. In some embodiments, the bolus calculator can be adapted to determine an insulin bolus as a function of glycemic index of the intake.

The following definitions are provided for terms used herein:
"GI" (Glycemic Index) refers to a ranking system for carbohydrates based on their effect on blood glucose levels.
"GL" (Glycemic Load) refers to the amount of carbs in a meal multiplied by the GI corresponding to that meal divided by 100.
"CIR" (Carbohydrates-to-Insulin-Ratio) refers to the amount of carbohydrates balanced by one unit of insulin.
"IS" (Insulin Sensitivity) refers to the amount of blood glucose value lowered by one unit of insulin.
"RI" refers to residual insulin, i.e. the amount of stored insulin remaining in the body post recent delivery of boluses that are still active.
"Dose" or "bolus dose" refers to amount of insulin administered to counteract carbohydrates in a meal.
"RIR" refers to the relative insulinemic response, which is the insulinemic response caused by a meal, expressed by the percentage of the insulinemic response after ingestion of a known amount of available carbohydrate from the GI reference food (e.g., 50 g glucose).
"AUC", or "glycemic response", refers to the area under the curve (AUC) of a plot of glucose concentration in plasma against time.
"RGR" refers to the relative glycemic response, which is the glycemic response caused by a meal, expressed by the percentage of the glycemic response after ingestion of a known amount of available carbohydrate from the GI reference food (e.g., 50 g glucose).

Referring to FIG. 5, a schematic diagram of an exemplary insulin infusion device 1000 is shown. The infusion device 1000 includes a dispensing patch unit 1010, which can be secured (e.g., adhered) to the user's skin 5, and a remote control unit 1008 which can communicate with the dispensing patch unit 1010 to enable, among other things, programming and communications of instructions (control and operations), user inputs and acquired data. The remote control unit 1008 may be implemented, in some embodiments, as a dedicated remote control. The remote control unit 1008 can also be implemented in a cell phone, a watch, a PDA, a laptop, an iPod and other devices having remote control and/or wireless functionalities. The remote control functionalities can be implemented using any number of wireless technologies, including, for example, RF-based devices IR-based devices and other types of electro-magnetic communications devices that implement suitable communication protocols (e.g., Bluetooth). In some implementations, the remote control unit 1008 can also communicate with controlled devices over a conductive wire.

The patch unit 1010 may generally be removable and connectable to a cannula 6 that penetrates the skin 5 to enable delivery of therapeutic fluids (e.g., insulin) to the patient. The patch unit 1010 can be attached to a cradle unit 20 that, in some embodiments, is a flat sheet (or plate) secured to the user's skin 5 to enable connection/disconnection of the patch unit 1010. An exemplary embodiment of this arrangement is described, for example, in co-owned, co-pending U.S. patent application Ser. No. 12/004,837 and International Application No. PCT/IL2007/001578, the contents of which are hereby incorporated by reference in their entireties.

Manual inputs may be provided, in some embodiments, using one or more buttons 1011 located on the dispensing patch unit 1010. The dispensing patch unit 1010 may include one or more housings. For example, in some embodiments, the dispensing patch unit includes a reusable part 1 and a disposable part 2, each having an associated housing. Further details regarding multi-part dispensing patch units are provided, for example, in co-owned, co-pending U.S. patent application Ser. No. 11/397,115 and U.S. Provisional Patent Application No. 61/123,509, the contents of which are hereby incorporated by reference in their entireties.

In accordance with some embodiments, the remote control unit 1008 may contain a bolus calculator 2000 to determine a bolus dosage to be administered, a processor 2010 (which may be used in the implementation of the bolus calculator 2000), a memory device 2020, a user interface that includes input interface unit 2030 a display 2040 and other indication and/or data entries units (not shown) such as audible and/or vibrational-based devices. The input interface unit 2030 may be provided to enable user input entry for use by the bolus calculator 2000 and/or for enabling dispensing patch unit 1010 programming.

The bolus calculator 2000 is configured to determine a recommend insulin bolus based on data pertaining to, for example, the current BG level, the carbohydrate load of the meal and the glycemic index of the meal. Such data may be obtained from sensing devices that measure and communicate the required data (e.g., a blood glucose sensor), or from information entered by a user through the user interface associated with the bolus calculator. In some embodiments, the bolus calculator may be located in the reusable part of the dispensing patch unit.

Figure 6:
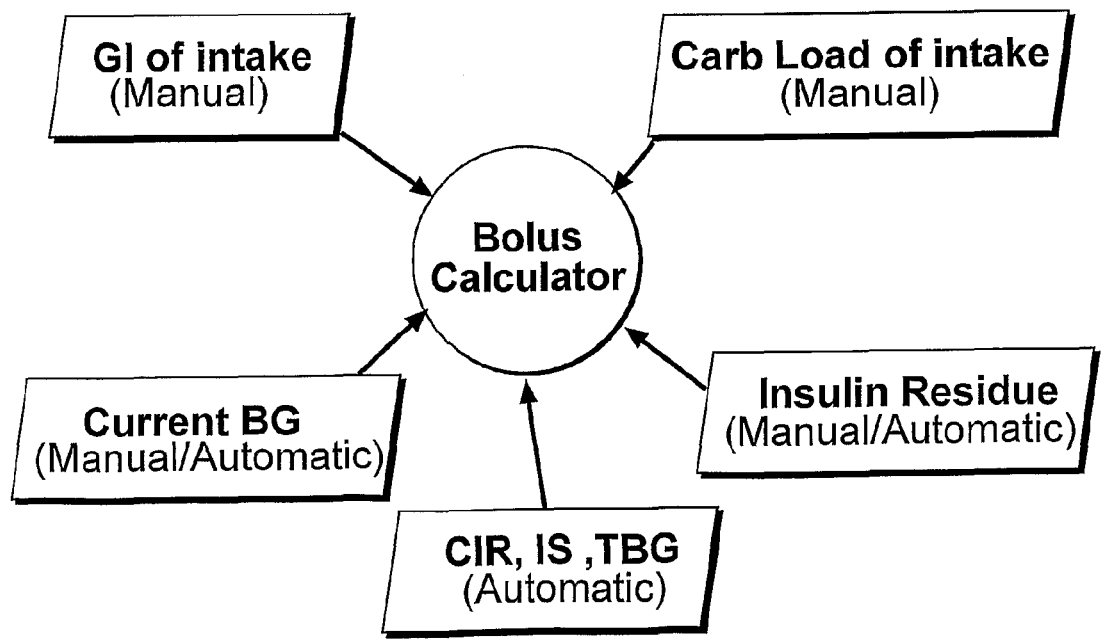
FIG. 6 is a diagram illustrating sample data acquisition modes for an exemplary bolus calculator.

Referring to FIG. 6, a diagram illustrating types of data inputs that may be received by a bolus calculator (e.g., the bolus calculator 2000 of FIG. 6), and based upon which a bolus dosage may be determined by the bolus calculator, is shown. Some of the data inputs may be provided manually (e.g., by a user entering the input data via a suitable user interface), while some of the data be acquired and communicated to the calculator automatically (e.g., using sensors to measure and communicate the particular data that may be used by the calculator). For example, the carbs load of the intake and the GI may be acquired manually (e.g., a user may enter the particular values pertaining to the carbs load and the GI associated with the food the user is to consume). On the other hand, the current blood glucose levels/or and the insulin residue may be acquired manually and/or automatically. Particularly, the blood glucose level of the user may be determined with the aid of a glucometer, a continuous subcutaneous glucose monitoring device, or any other suitable sensing device to measure blood glucose levels.

In some embodiments, the device may comprise a glucometer that is in communication with the bolus calculator to enable direct communication of the measured blood glucose to the bolus calculator. In some embodiments, a communication channel may be established between the bolus calculator and an independent glucometer to enable direct receipt of the measured blood glucose.

In some embodiments, a continuous subcutaneous glucose monitoring apparatus can continuously and/or periodically transmit BG levels to the bolus calculator. In some implementations, the bolus calculator may be electrically coupled to an independent continuous subcutaneous glucose monitoring device (e.g., via a wire) to enable direct transmission of electrical signals representative of the measured blood glucose to the bolus calculator.

Data pertaining to the residual insulin (time and dose of last boluses) may be obtained manually and/or automatically, thus enabling computation of the appropriate amount of the bolus dose that needs to be administered (e.g., the residual insulin may be required to be known so that the patient does not receive an excessive amount of insulin bolus). The carbohydrate-to-insulin ratio (CIR), insulin sensitivity (IS), and target blood glucose (TBG) can be entered as initial settings of the user into the bolus calculator. These values may be treated as constant parameters in subsequent calculations, or one or more of those parameters may be adjusted (through subsequent manual entry via the user interface, through remote data transmission to a communication module included with the device, etc.)

The insulin bolus dose that is to be calculated is dependent, at least in part, on the predicted glycemic response, and can be determined as a function of the carbohydrate load of the intake and of the glycemic index of the carbohydrate load.

The glycemic response, corresponding to the area under the curve (AUC) of a plot of glucose concentration in plasma against time, has been demonstrated to be a function of the carbohydrate load of the intake and of the glycemic index of the carbohydrate load. For example, the area under the curve can be determined using the relationship: AUC=1.5*carbs+ 1.4*GI−46, where carbs is the amount of carbohydrates provided in grams, and GI is the glycemic index of the carbs (see, for example, Am J Clin Nutr 2006; 83; 1306-12).

The insulinemic response of healthy subjects caused by the consumption of a meal, which may be expressed as a percentage of the insulinemic response after ingestion of 50 g available carbohydrate from the GI reference food, is referred to as the "relative insulinemic response" (RIR). As explained, for example, in the reference Am J Clin Nutr 2006; 83; 1306-12, the RIR may be computed (represented by the following equation:

$$RIR = 2.9*(0.6*GI + 0.003*GI2)*(1 - e^{-0.00788*carbs}) + 5.$$

Figure 7:
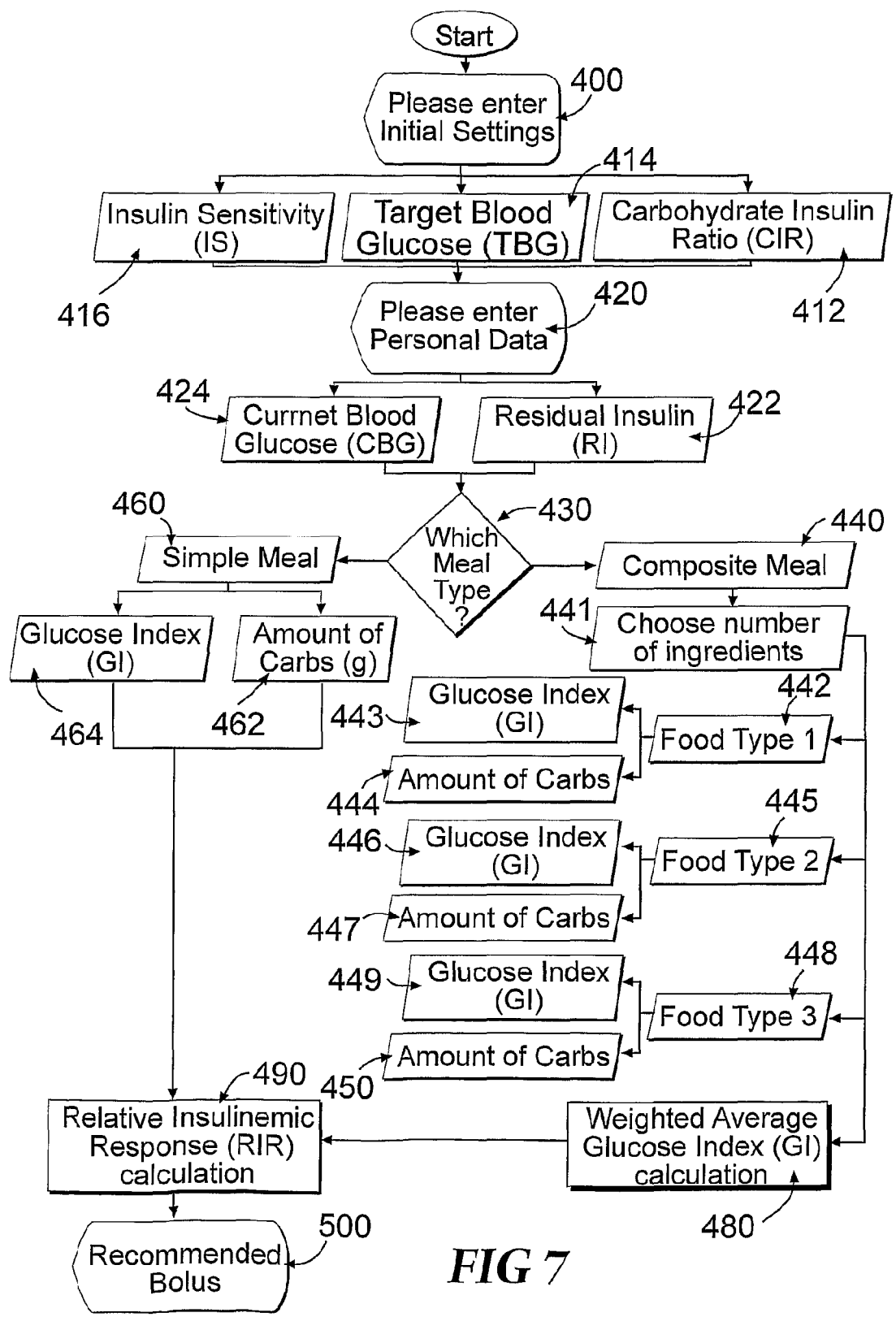
FIG. 7 is a flowchart of an exemplary bolus level determination procedure to compute bolus dosage levels.

Referring to FIG. 7, a flowchart of an exemplary bolus level determination procedure is shown. Initially, user-dependent parameters, such as target blood glucose (TBG) 414, insulin sensitivity (IS) 416 and carbohydrate to insulin ratio (CIR) 412 are inputted 400 into the system. Current clinical user data, such as the current blood glucose (e.g., CBG before consumption of a meal) 424 and the amount of residual insulin (RI) 422 from previous bolus administrations are provided 420 to the system. These values may be determined automatically by one or more sensors coupled to or in communication with the system implementing the bolus calculator, and provided thereto.

The calculator may subsequently receive information from the user regarding the meal type that is to be consumed, and thus a determination is made 430 as to whether the meal is a simple meal (e.g., the dietary content of the meal can be represented as a single set of a carbs amount and a corresponding glycemic index associated with that meal), or whether the meal type is of a composite type (e.g., the dietary content is composed of multiple components that need to be individually represented by respective sets of carbs amounts and glycemic indices). If it is determined that the meal type is a simple meal (represented as block 460), the glucose index 464 and amount of carbs 462 for that simple meal are provided to the calculator. In some embodiments, the actual data corresponding to the required information is provided by the user, or alternatively, a specific description of the food may be provided, and the corresponding GI and carbs for that food retrieved from a table or food database stored on a memory device coupled to the calculator. The information pertaining to the meal to be consumed and/or its dietary content may also be communicated from a remote location (e.g., via a wireless communication system), etc. Thus, in some embodiments, the table or database may be stored on a memory device of a remote system (e.g., processor-based server) and communicated to the calculator in response to a request sent to that remote system to provide the required data.

If the meal is a composite meal (represented by block 440 in FIG. 7), the constituents (or ingredients) of the composite meal are determined 441 by, for example, having the user specify, through the user interface, the constituents of the meal (e.g., steak, mashed potatoes, sour cream, etc.), or having the calculator, or some other processor-based module, determine the constituents based on a generic description of the composite meal (e.g., a steak dinner). Having determined the constituents of the composite meal, the respective carbs amount and glycemic index for each constituents are provided (at 442-450). Particularly, similar to the determination of the carbs and GI for a simple meal, the carbs and GI values for the various constituents of the composite meal specified may be provided by the user him/herself (e.g., by entering those value individually for each constituent), or by the bolus calculator retrieving the data from tables/database stored on a local memory device coupled to the calculator, or by sending a request (via, e.g., a wireless channel, or a network connection) to a remote system on which the carbs/GI values are stored.

In circumstances where a composite meal is to be consumed, the weighted average of the glycemic index of the meal is determined 480. This is followed by determining 490 the relative insulinemic response (RIR), which is applied for the final bolus dose computation 500.

Figure 8:
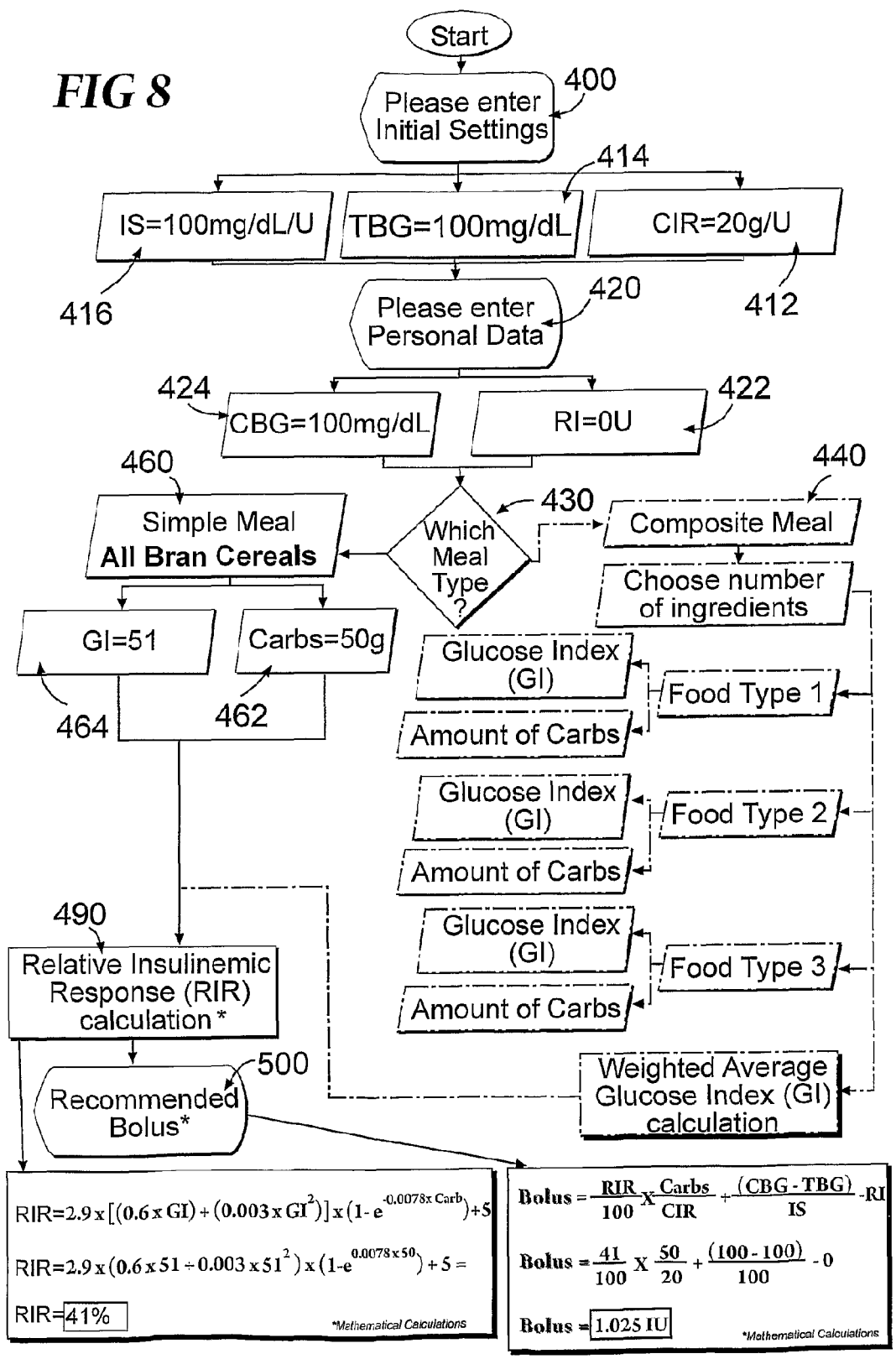
FIG. 8 is a flowchart of the exemplary bolus level determination procedure of FIG. 7 showing an exemplary computation of a bolus level recommendation by, for example, the bolus calculator.

Referring to FIG. 8, a flowchart of an example of a bolus dose determination performed by the bolus calculator in accordance with, for example, the procedure depicted in FIG. 7, is shown. In this example, the user has a TBG of 100 mg/dL (which the user may have entered 414 using the user interface), a CIR of 20 g/U (entered, for example, at 412) and an IS of 100 mg/dL/U (entered at 416). In this example, the user consumes a simple meal (as determined at 430) comprising one food type, having 50 grams carbohydrates (as specified, for example, at 462) and a glycemic index of 51 provided at 464 (the GI value may have been obtained by accessing a table, similar to the table of FIG. 4, stored on a local or remote memory device). Also provided to the calculator is an indication that there is no residual insulin from previous boluses (at 422) and information that the user's current BG equals his target BG (at 424).

Having obtained and/or determined the above parameters, the bolus calculator determines 490 the relative insulinemic response of the meal to be 41% by performing, for example, the computation provided in Equation 3, above. Using the RIR value thus determined, the Bolus that is to be delivered is determined (using, for example, Equation 2, above) to be 1.025 IU (500). Had the relatively low glycemic index of the consumed intake not been considered, the bolus that would have been recommended by currently available bolus calculators would have been computed based on the relationship of carb/CIR, and thus determined to be 2.5 IU. Consequently, 1.485 IU extra units would have been recommended under those circumstances when the GI of the intake was not to be considered, exposing the user to potential hypoglycemia.

Figure 9:
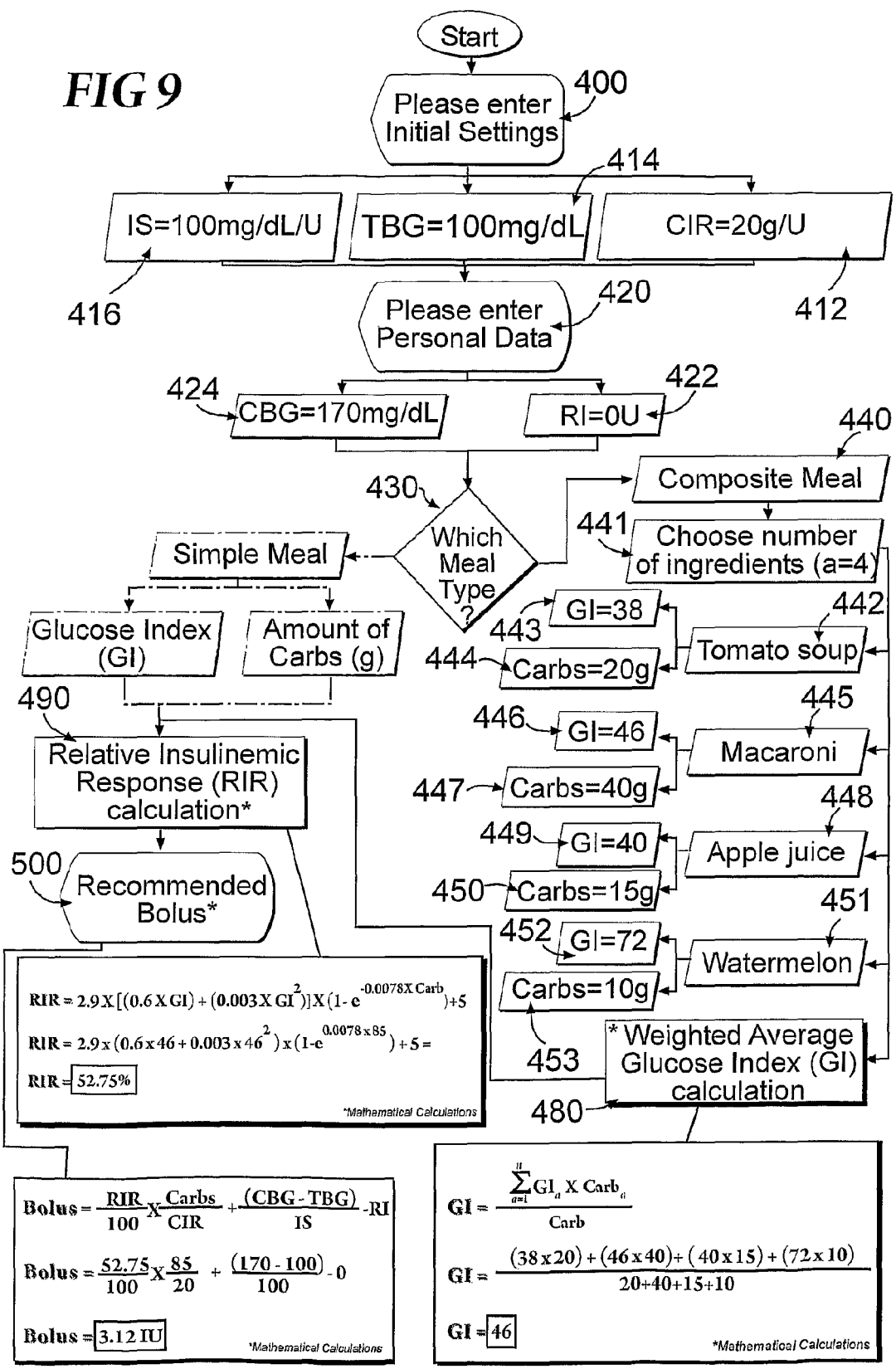
FIG. 9 is a flowchart of the exemplary bolus level determination procedure of FIG. 7 showing another exemplary computation of bolus level recommendation by, for example, the bolus calculator.

Referring to FIG. 9, a flowchart depicting another example of a bolus dose determination performed by the bolus calculator in accordance with, for example, the procedure depicted in FIG. 7, is shown. The user of the example has a TBG of 100 mg/dL (which the user may have entered 414 using a user interface), a CIR of 20 g/U (entered at 412) and an IS of 100 mg/dL/U (entered at 416). In this particular example, there is no residual insulin from previous boluses (as indicated at 422) and the user's current BG is higher than the target BG (as provided at 424).

The user of the example consumes a composite meal (as indicated at 440) comprising four (4) elements (or constituents), as specified at 441, namely:
  tomato soup (specified at 442) comprising 20 grams carbohydrates (specified at 444) and glycemic index of 38 (specified at 443);
  macaroni (specified at 445) comprising 40 grams carbohydrates (specified at 447) and glycemic index of 46 (specified at 446);
  apple juice (specified at 448) comprising 15 grams carbohydrates (specified at 450) and glycemic index of 40 (specified at 449); and
  watermelon (specified at 451) comprising 10 grams carbohydrates (specified at 453) and glycemic index of 72 (specified at 452).

The weighted average of the glycemic index of the entire meal is determined 480, by performing the computation of, for example, Equation 1 above, to be 46. The relative insulinemic response of the meal is therefore determined 490, by performing, for example, the computations of Equation 3 above, to be 52.75%. The Bolus to be delivered is therefore determined 500, in accordance with computations based on application of Equation 2 above, to be 3.12 IU. Had the relatively low glycemic index not been considered, the bolus that would have been recommended by currently available bolus calculators would have been computed based on the relationship carb/CIR+(CBG−TBG)/IS, and would thus have been determined to be 4.95 IU (85/20+(170−100)/100=4.25+ 0.7=4.95 IU). As a result, 1.83 IU extra units would have been recommended had the GI of the intake not been considered.

Figure 10:
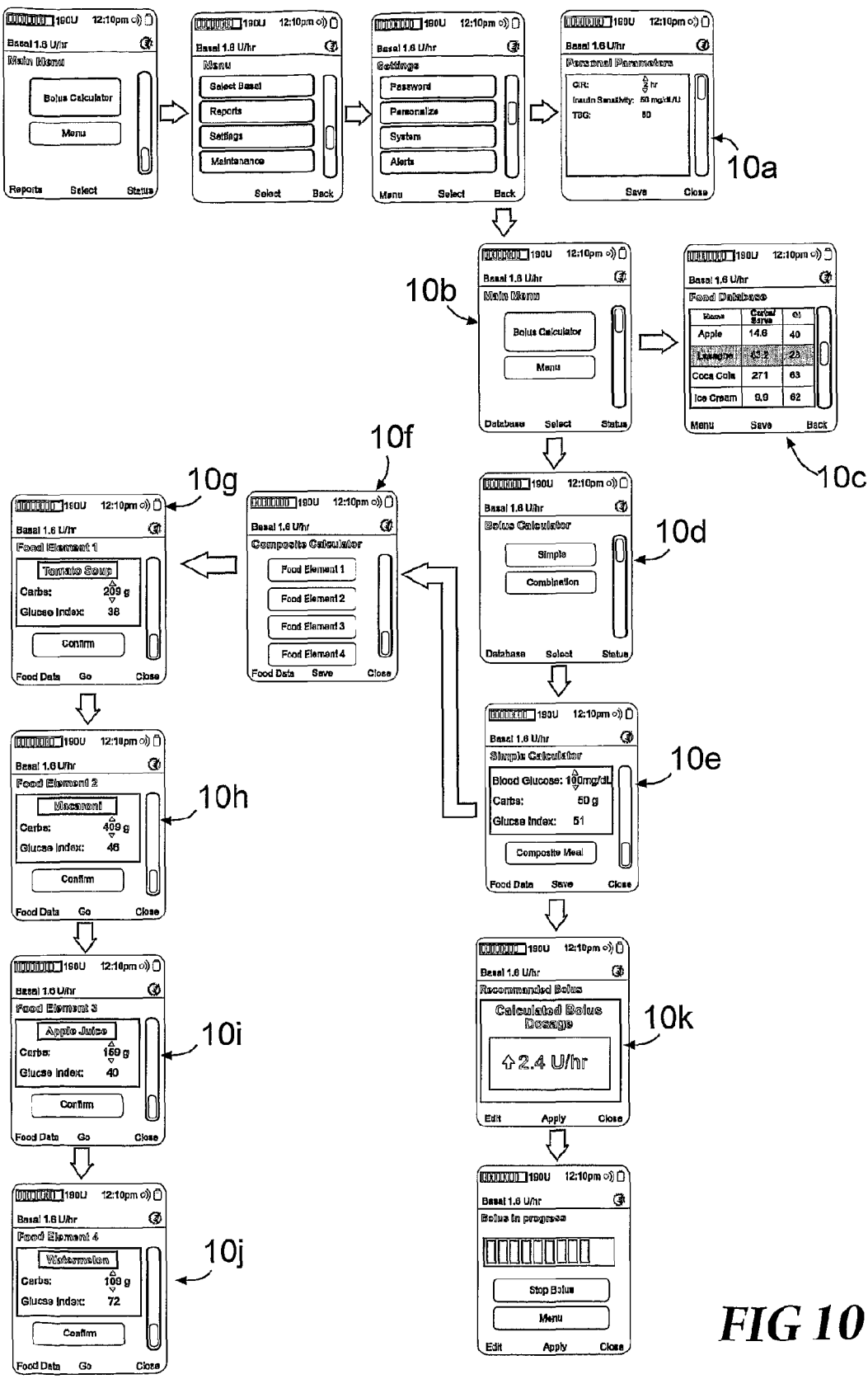
FIG. 10 is a flow diagram of an exemplary bolus calculator user interface screens.

Referring to FIG. 10, a flow diagram of bolus calculator user interface screens is shown. In some implementations, the user interface depicted can be implemented using navigation windows for data input. FIG. 10*a* illustrates examples of windows for inputting carbohydrate-to-insulin ratio (CIR), insulin sensitivity (IS), and target blood glucose (TBG).

According to some embodiments (not shown in FIG. 10), the user can also input the rules corresponding to the IS value and the CIR. For example, some users may use the "1800 Rule" to calculate it, while others may use the "1600 Rule". The rule applied may be determined as a function of the percentage of basal insulin from the total daily dose. In some implementations, the CIR and IS can be periodically reassessed according to the total daily insulin dose (TDD) stored, for example, in the memory of the device. The rules can also be periodically reassessed according to the percentage of the basal insulin of the TDD, as saved in the memory of the device (the higher the percentage of basal insulin from the TDD, a higher rule number should be applied).

FIG. 10*e* illustrates an example of a window for inputting current blood glucose levels, carbohydrate load of the intake, and GI of the intake. The "composite" button can be selected for calculations involving meals with multiple food elements (constituents), having different carbohydrate loads of the intake and GI. For example, the windows illustrated in FIGS. 10*f-j* can be used for inputting food element information for tomato soup, macaroni, apple juice and watermelon.

The user can enter a food database window (as shown in FIG. 10*c*) displaying the carb load and GI of different foods via the windows depicted in FIG. 10*b, d-j*. FIG. 10*k* provides an example of a window (screen) displaying a recommended bolus dose. FIG. 10*b* provides an example of a main window of the bolus calculator. Additional windows (screens) may be accessible via the main window (e.g., a window for downloading the last bolus data).

Figure 11A:
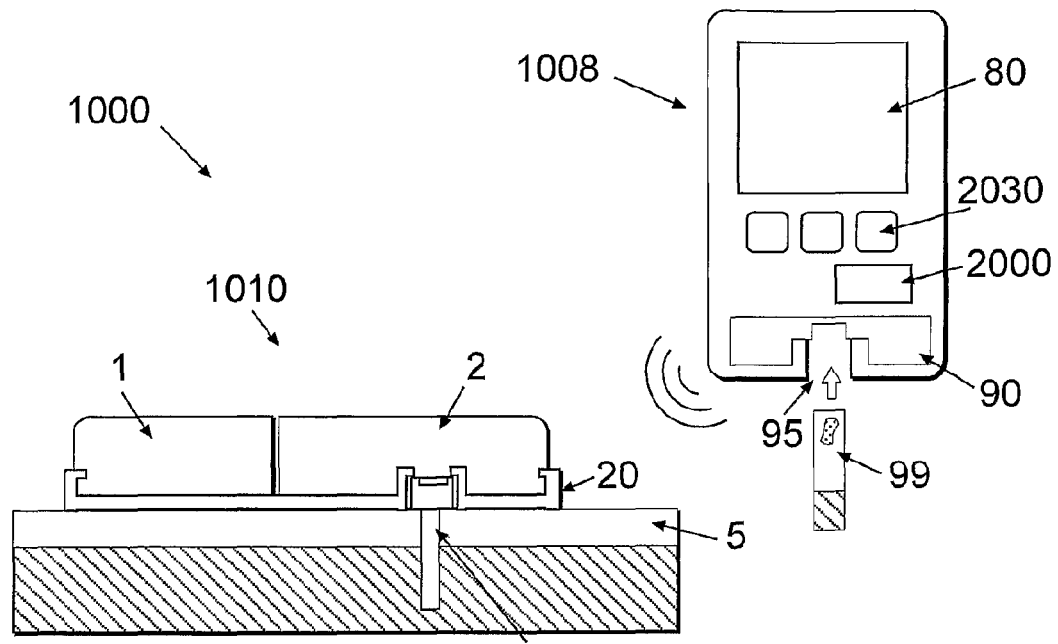
FIGS. 11*a-c* are schematic diagram of exemplary insulin infusion devices that include blood glucose monitors (in three different locations) to provide blood glucose (BG) readings for a bolus calculator.

Referring to FIG. 11, schematic diagrams of three exemplary embodiments of an insulin infusion device are shown. Each of the exemplary devices contains a glucometer 90 to be used to measure blood glucose (BG) and provide it as input to the bolus calculator 2000. Particularly, FIG. 11*a* shows a glucometer 90 located in the remote control unit 1008 of the device. The glucometer 90 includes an opening 95 for receiving of a test strip 99. For example, the user can extract blood from the body, place the blood on the test strip 99 and insert the strip into the opening 95. The glucose readings 90 may be displayed on, for example, a screen 80 of the remote control unit 1008.

Figure 11B:
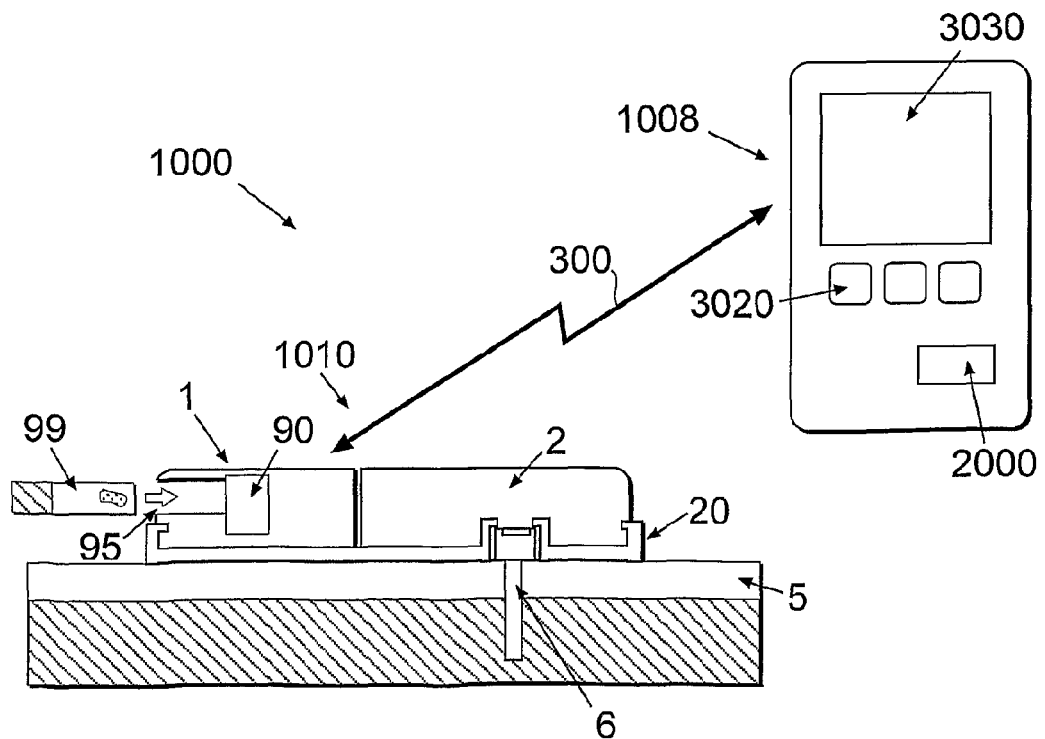
Figure 11C:
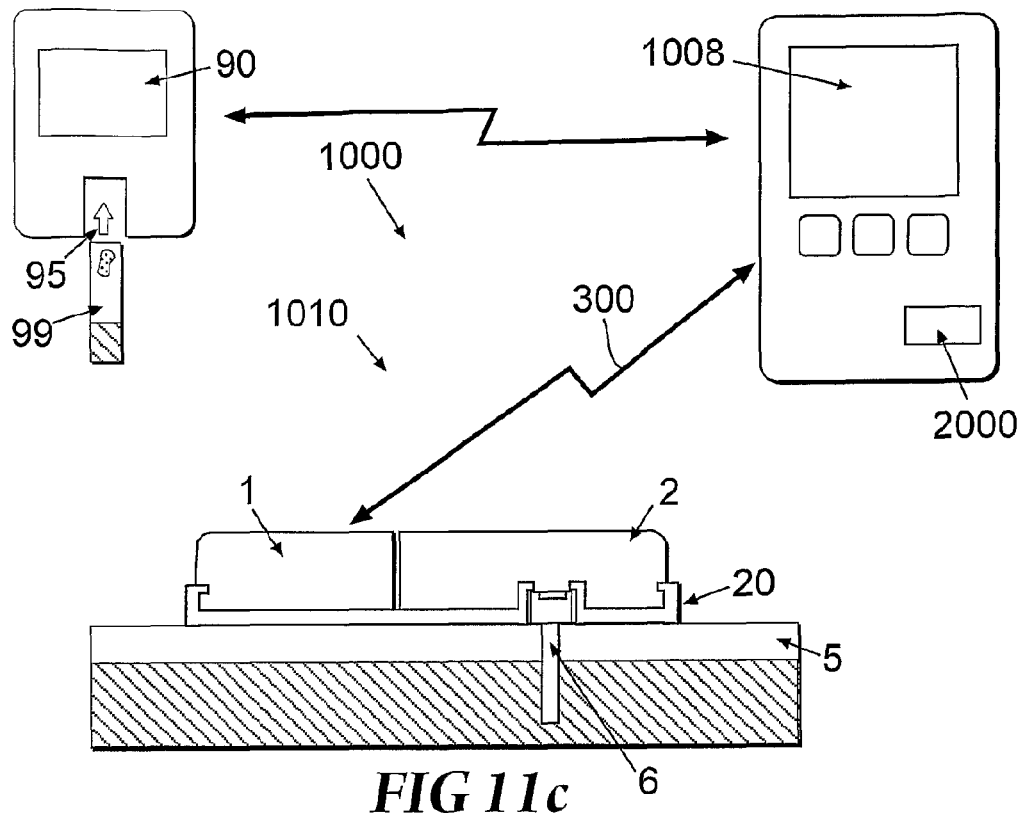

FIG. 11*b* shows a glucometer 90 located in a reusable part 1 of the dispensing patch unit 1010. A communication channel 300 between the glucometer 90 located in the dispensing patch unit 1010 and the bolus calculator 2000 residing, for example, in the remote control unit 1008, may be established and maintained, thus enabling device programming, data acquisition and handling, and communication of user inputs. FIG. 11*c* shows an embodiment in which glucose readings can be directly or remotely received from an independent glucometer 90.

Figure 12A:
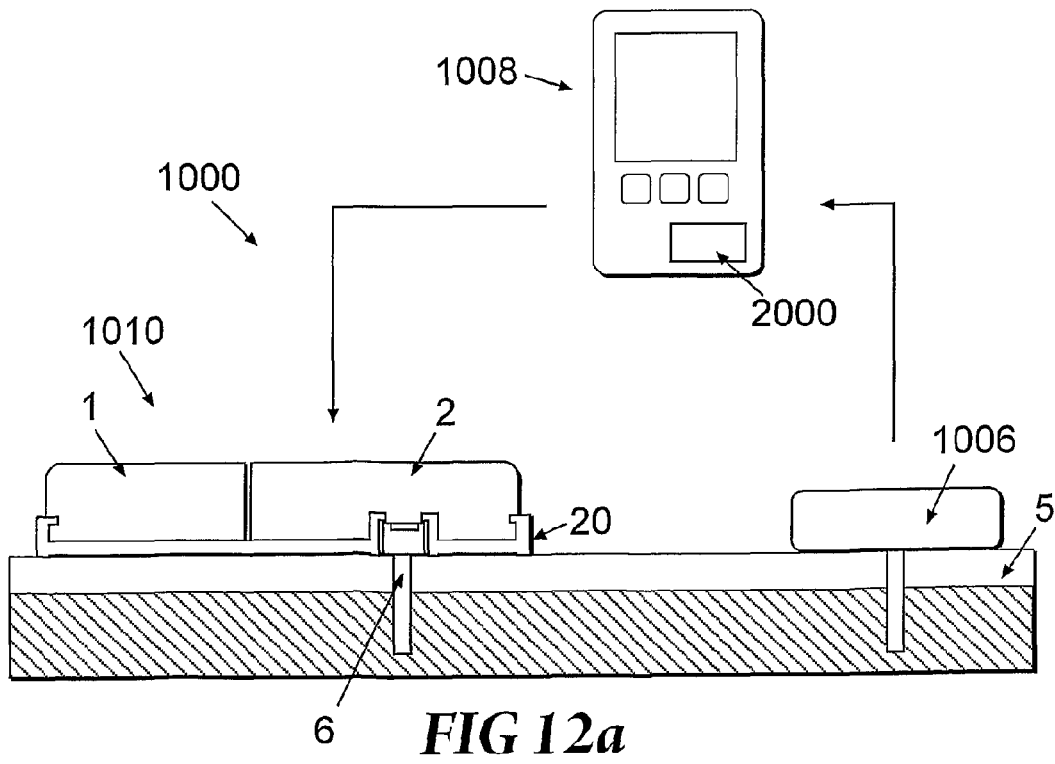
FIGS. 12a-b are schematic diagrams of two embodiments of insulin infusion devices containing continuous subcutaneous glucose monitors to provide blood glucose readings (BG) for a bolus calculator.
Figure 12B:
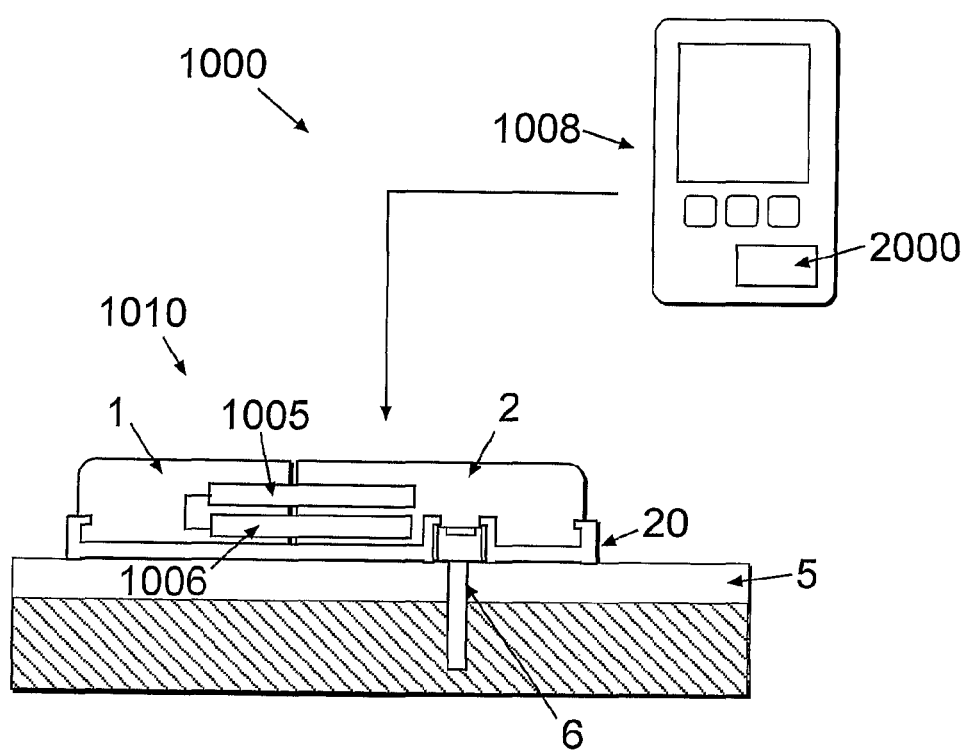

Referring to FIGS. 12*a-b*, schematic diagrams of exemplary insulin infusion devices that continuous subcutaneous glucose monitors 1006 to provide blood glucose readings to a bolus calculator. A communication channel between the continuous subcutaneous glucose monitor 1006 and the bolus calculator 2000 residing in the remote control unit 1008 can be established and maintained, for example, to enable device programming, data acquisition and handling, and communication of user inputs.

Particularly, FIG. 12*a* shows an embodiment in which the current blood glucose concentration can be received from an independent continuous subcutaneous glucose monitor 1006 and manually or automatically entered by a patient to the bolus calculator 2000.

FIG. 12b shows an embodiment in which a continuous subcutaneous glucose sensing apparatus 1006 can be located in the dispensing patch unit 1010 of the insulin delivery device.

As described, for example, in co-owned, co-pending U.S. patent application Ser. Nos. 11/706,606 and 11/963,481, and in International Patent Application No. PCT/IL07/001,579, the contents of which are hereby incorporated by reference in their entireties, the insulin dispensing apparatus 1005 and glucose sensing apparatus 1006 can constitute a single delivery device, and may also use a single cannula 6 to perform or facilitate the dispensing and sensing functionalities. Alternatively (not shown), the sensing apparatus and the dispensing apparatus can have separate canulas that penetrate the skin 5 and reside in the subcutaneous tissue. In some embodiments, the glucose sensing apparatus can be implemented with dynamic range of sensing frequencies. For example, the glucose sensing can be continuous, semi-continuous, periodic or discrete. The sensing frequencies can be pre-programmed to have a default value. The sensing frequencies can also be controlled by the user.

In some embodiments, the device may be implemented as a closed loop or semi closed loop system. Insulin can thus be automatically dispensed according to continuous monitoring and additional pre-meal bolus user inputs (semi-closed loop). The bolus calculator 2000 can be used for bolus inputs in the semi closed loop system.

Various implementations of the subject matter described herein may be realized in digital electronic circuitry, integrated circuitry, specially designed ASICs (application specific integrated circuits), computer hardware, firmware, software, and/or combinations thereof. These various implementations may include implementations in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any computer program products, apparatus and/or devices (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube), LCD (liquid crystal display) monitor and/or other types of display devices) for displaying information to the user, as well as a keyboard, a pointing device (e.g., a mouse or a trackball) and/or other types of user input devices through which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

Although a few variations have been described in detail above, other modifications are possible. For example, the logic flow depicted in the accompanying figures and described herein does not require the particular order shown, or sequential order, to achieve desirable results. Other implementations may be within the scope of the following claims.

What is claimed is:

1. A medical device to treat diabetes, the medical device comprising:
   a processor;
   a bolus calculator comprising computer instructions that, when executed by the processor, cause the processor to perform operations comprising:
      receiving a meal type corresponding to a food intake to be consumed by a user, the meal type can be a first meal type representing a simple meal or a second meal type representing a composite meal;
      receiving a plurality of food types associated with the food intake to be consumed by the user if the second meal type is received;
      calculating a bolus to be delivered to the user for the food intake to be consumed by the user; the bolus being calculated based, at least in part, on:
         the meal type, a carbohydrate load of the food intake to be consumed by the user if the first meal type is received, the plurality of food types associated with the food intake to be consumed by the user if the second meal type is received, a current glucose level of the user, a residual insulin of the user, a carbohydrate-to-insulin ratio of the user, an insulin sensitivity of the user, and a target glucose level of the user;
   wherein the processor is housed in one or more of:
      an insulin dispensing pump, a handheld remote control for the insulin dispensing pump and a handheld glucose monitor;
   and wherein the computer instructions further include instructions to reevaluate an effect of the carbohydrate load based on a value associated with a glycemic index of the food intake.

2. The medical device of claim 1, further comprising a user interface configured to receive at least one or more of: the carbohydrate load if the first meal type is received, the meal type, the plurality of food types associated with the food intake to be consumed by the user if the second meal type is received, the glycemic index, the value associated with the glycemic index, the current glucose level, the residual insulin, the carbohydrate-to-insulin ratio, the insulin sensitivity, and the target glucose level.

3. The medical device of claim 1, further comprising a user interface configured to display to the user one or more of: the calculated bolus, a food database, the glycemic index, the value associated with the glycemic index, a meal selection, a composite glycemic index, the carbohydrate load if the first meal type is received, the current glucose level, the residual insulin, the carbohydrate-to-insulin ratio, the insulin sensitivity, and the target glucose level.

4. The medical device of claim 1, wherein at least some of the food types have different glycemic indices.

5. The medical device of claim 1, further comprising:
a user interface configured to receive input of the meal type corresponding to the food intake to be consumed by the user and the food types associated with the food intake to be consumed if the second meal type is received, each of the food types being associated with a respective glucose index and a respective amount of carbohydrates;
wherein the computer instructions further comprise instructions to determine a weighted average glucose index based on the respective glucose index and the respective amount of carbohydrates of each of the food types if the second meal type is received.

6. The medical device of claim 1, further comprising a memory storing a food database including glycemic indices corresponding to a plurality of food intakes, the bolus calculator being configured to retrieve at least the glycemic indices.

7. The medical device of claim 1, further comprising the insulin dispensing pump, wherein the bolus calculator is used in conjunction with the processor of the pump to dispense insulin to the user in correspondence with the calculated bolus.

8. The medical device of claim 1, further comprising the glucose monitor configured to measure the current glucose level of the user.

9. The medical device of claim 1, wherein the processor operating the bolus calculator is located in the handheld remote control.

10. The medical device of claim 1, wherein the value associated with the glycemic index of the food intake is multiplied by the carbohydrate load.

11. The medical device of claim 1, wherein the value associated with the glycemic index (GI) of the food intake is associated with a relative insulinemic response (RIR) computed based on:

$$RIR = 2.9*(0.6*GI + 0.003*GI^2)*(1 - e^{-0.0078*carb}) + 5$$

wherein carb is the carbohydrate load of the food intake.

12. The medical device of claim 1, wherein the computer instructions further comprise instructions to calculate the bolus based on a relationship:

$$Bolus = \frac{RIR}{100} * \frac{carb}{CIR} + \frac{CBG - TBG}{IS} - RI$$

wherein RIR is the a relative insulinemic response computed based on a relationship:

$$RIR = 2.9*(0.6*GI + 0.003*GI^2)*(1 - e^{-0.0078*carb}) + 5$$

and wherein CIR is the carbohydrate to insulin ratio of the user, IS is the insulin sensitivity of the user, CBG is the current glucose level of the user, TBG is the target glucose of the user, RI is the residual insulin from previous insulin administration to the user, GI is the glycemic index of the food intake, and carb is the carbohydrate load of the food intake.

13. The medical device of claim 1, wherein if the second meal type is received, the computer instructions further comprise instructions to determine a composite glycemic index based on respective glycemic indices and carbohydrate loads of the plurality of food types.

14. The medical device of claim 13, wherein the composite glycemic index is determined based on:

$$GI = \frac{\sum_{a=1}^{n} GI_a * Carb_a}{Carb}$$

wherein GI is the composite glycemic index for the composite intake, n is a number of carbohydrate-containing dietary components in the composite intake, $GI_a$ is an individual glycemic index GI of an $a^{th}$ dietary component, Carb is a carbohydrate load of the entire composite intake and $Carb_a$ is an individual carbohydrate load of the $a^{th}$ component of the composite intake.

15. The medical device of claim 1, wherein the current glucose level includes one or more of: a blood glucose level of the user and a glucose level in interstitial fluids of the user.

16. The medical device of claim 1, further comprising a screen to display to the user one or more of: the calculated bolus, a food database, the glycemic index, the value associated with the glycemic index, and a meal selection.

17. A method for treating diabetes, the method comprising:
providing a processor housed in at least one of an insulin dispensing pump, a handheld remote control for the insulin dispensing pump and a handheld glucose monitor;
providing a bolus calculator application comprising computer instructions for operating on the processor to determine a bolus for delivery to a user;
receiving input comprising a meal type corresponding to a food intake to be consumed by the user, the meal type can be a first meal type representing a simple meal or a second meal type representing a composite meal, a carbohydrate load of a food intake to be consumed by the user if the first meal type is received, a plurality of food types associated with the food intake to be consumed by the user if the second meal type is received, a current glucose level of the user, a residual insulin of the user, a carbohydrate-to-insulin ratio of the user, an insulin sensitivity of the user, and a target glucose level of the user;
determining the bolus based at least in part on the carbohydrate load of the food intake to be consumed by the user if the first meal type is received, the plurality of food types associated with the food intake to be consumed by the user if the second meal type is received, the current glucose level of the user, the residual insulin of the user, the carbohydrate-to-insulin ratio of the user, the insulin sensitivity of the user, and the target glucose level of the user; and
reevaluating an effect of the carbohydrate load based on a value associated with a glycemic index of the food intake.

18. The method of claim 17, further comprising receiving input to select the food intake having the associated glycemic index.

19. The method of claim 17, further comprising providing the insulin dispensing pump, wherein the bolus calculator application is used in conjunction with the processor of the pump to dispense insulin to the user in correspondence with the determined bolus.

20. The method of claim 17, further comprising multiplying the value associated with the glycemic index of the food intake by the carbohydrate load.

* * * * *